United States Patent [19]

Parks et al.

[11] Patent Number: 4,510,244

[45] Date of Patent: Apr. 9, 1985

[54] CELL LABELING WITH ANTIGEN-COUPLED MICROSPHERES

[75] Inventors: David R. Parks, Stanford; Virginia M. Bryan, San Carlos; Leonard A. Herzenberg, Stanford, all of Calif.

[73] Assignee: The Board of Trustees of the Leland Stanford Jr. University, Stanford, Calif.

[21] Appl. No.: 421,668

[22] Filed: Sep. 22, 1982

Related U.S. Application Data

[63] Continuation of Ser. No. 141,031, Apr. 17, 1980, abandoned.

[51] Int. Cl.$^3$ ............... C12N 15/00; C12N 5/00; C12P 21/00; G01N 33/54
[52] U.S. Cl. .................. 435/172.2; 435/68; 435/240; 435/7; 436/533; 436/534; 436/546; 436/548; 436/824; 436/519
[58] Field of Search ............ 435/7, 68, 172, 241, 435/240, 172.2; 436/548, 526, 527, 531, 533, 534, 544, 545, 546, 824, 800, 804, 805, 806, 519

[56] References Cited

U.S. PATENT DOCUMENTS

| | | | |
|---|---|---|---|
| 4,108,972 | 8/1978 | Dreyer | 436/533 |
| 4,172,124 | 10/1979 | Koprowski et al. | 435/240 |
| 4,196,265 | 4/1980 | Koprowski | 435/68 |
| 4,284,412 | 8/1981 | Hansen et al. | 422/82 |
| 4,363,799 | 12/1982 | Kung et al. | 435/7 |

OTHER PUBLICATIONS

Liesegang et al., P.N.A.S. USA, 75(8):3901–3905 (1978).
Melchers et al., Current Topics in Microbiology and Immunology, 81, Springer-Verlag, New York, IX–XXIII (1978).

Primary Examiner—Esther M. Kepplinger
Attorney, Agent, or Firm—Bertram I. Rowland

[57] ABSTRACT

Method for isolating specific antibody hybridomas from a hybridoma cell mixture employing antigen-conjugated labeled microspheres and a label activated cell sorter. By selecting for labeled cells which produce light scatter and low red autofluorescence, viable single cells can be isolated and cloned which produce the desired antibodies.

5 Claims, No Drawings

CELL LABELING WITH ANTIGEN-COUPLED MICROSPHERES

CROSS-REFERENCE TO RELATED APPLICATIONS

This application is a continuation of copending parent application Ser. No. 141,031, filed Apr. 17, 1980, now abandoned.

BACKGROUND OF THE INVENTION

1. Field of the Invention

The recent development of myeloma-hybrid cell lines for producing immunospecific antibodies allows for the indefinite production of large quantities of homogeneous (monoclonal) antibody specific for a single antigenic determinant of an immunizing antigen, despite the overall heterogeneity of the antibody response to the antigen. Cloning and selecting lines with desired reactivities, however, is currently a laborious procedure that constitutes a major limitation to rapid establishment of a wide range of lines producing antibodies useful for research and medicine.

The current selection procedures rely on dispersion of cells in soft agar or on limiting dilution microculture for physical isolation of the hybrid clones after hybridization. Desired hybrids are identified by screening for production of antibody after clones grow. For many antigens not readily adapted to a plaque assay, such as protein antigens, allotypes and impure mixtures of naturally occurring antigens, culture supernates are assayed for antibody. There are practical limits to the number of individual culture supernates which may be screened. Furthermore, besides the difficulties in screening large number of isolates to find the desired clone(s), there is the further difficulty that overgrowth of the culture by unwanted clones or nonproducing variants may obscure the desired clone.

It is therefore desirable that a rapid, accurate and efficient method be provided for screening large numbers of cells, either existing individually or as part of a clone, for isolating one or more hybridoma cells producing the desired antibody.

2. Description of the Prior Art

Parks et al., PNAS USA (1979) 76, 1962–1966 describes the subject process and its disclosure is incorporated herein by reference. Of interest to the background of the subject invention are the references cited therein.

SUMMARY OF THE INVENTION

Rapid and efficient isolation of viable hybridoma cells producing a desired antibody is achieved by combining a mixture of cells with antigen-bound labeled e.g. fluorescent particles under conditions where the cells bind to the particles. The mixture is then subjected to a fluorescence-activated cell sorter and the individual fluorescent cells isolated from the other cells. Desirably, the sorter further selects for viable cells by including light scattering and autofluorescence (red) as selection parameters.

DESCRIPTION OF THE SPECIFIC EMBODIMENTS

A rapid and efficient method for segregating hybridoma cells producing a desired antibody is achieved by combining a mixture of hybridoma cells capable of producing a plurality of different antibodies with antigen bound labeled particles under conditions where the particles bind to the cells having antibodies homologous to the antigens.

The mixture is then introduced into a label activated cell sorter, which allows for discrimination between individual labeled and unlabeled cells, as well as degree of labeling. Various labels include fluorescent labels, in relatively high numbers as microspheres, ferromagnetic labels, ionic charges, radioactive labels, or the like. Since fluorescence activated cell sorters are available and have shown to be capable of a high selective efficiency and discrimination, the subsequent description will be directed to the use of fluorescence.

With fluorescence used for selection the hybridoma mixture will be combined with fluorescent microspheres. The mixture is then introduced into a fluorescence-activated cell sorter which provides for excitation and fluorescent emission measurement to detect those cells to which at least one, more usually a plurality, of microspheres are specifically bound. The cells are segregated and may then be cloned to provide for production of monoclonal antibodies. Preferably, the cell sorter also allows for selection of viable cells, so that only viable hybridoma cells providing the desired antibody are segregated. The resulting segregated hybridomas may then be cloned and the desired antibody isolated from the supernatant of the nutrient medium.

The two materials employed in the subject invention are the hybridoma cells and the antigen-coupled fluorescent microspheres.

The hybridoma cells may be produced by any technique which provides for a clone capable of producing antibodies specific for a determinant site. The hybridoma cells are viable in vitro and are capable of multiplication and maintenance of production of the specific antibody. For a description of the preparation of hybridoma cells, see for example Herzenberg et al. (1978) *In Handbook of Experimental Immunology*, ed. Weir, D. M. (Blackwell, Oxford) Third ed. pages 25.1–25.7).

The fluorescent microspheres may be varied widely as to composition, being generally in the size and in the range of about 0.25 to 2 $\mu$M diameter, more usually about about 0.5 to 1 $\mu$M. The microspheres will normally be made of an inert material and include a plurality of fluorescent chromophoric functionalities, usually absorbing above about 400 nm, preferably absorbing above about 450 nm. The microspheres will have a high concentration of fluorescent functionalities to provide for a large signal per microsphere. The concentration of fluorescent functionalities will be primarily a matter of convenience, the minimum concentration being one which allows for discrimination of the microsphere bound cells.

Various organic polymers may be employed for the microspheres, e.g. polystyrene, polymethacrylate, or the like or inorganic polymers, e.g. glass or combinations thereof. The particular choice of the polymeric composition is primarily one of convenience, so long as the particles are not strongly adsorbing, do not interfere with the light absorption and fluorescent measurements of the complex of the particle and cell and provide a means for binding, either directly or indirectly, the specific determinant site for the desired monoclonal antibody. Conveniently, a broad range of fluorescent microspheres are commercially available, which have a plurality of functionalities, e.g. amino, carboxy, imino, or the like, for covalently bonding the antigen to the microsphere surface.

It should be appreciated, of course, that in referring to antigens, it is not intended to exclude haptens, the subject invention being useful for ligands generally.

The weight ratio of ligand to microsphere may vary widely, varying from about $1 \times 10^{-3}:1$ to about $0.5:1$, more usually from about $0.01-0.1:1$. The criteria governing the number of ligands bound to the microsphere will be the availability of the ligand, the size of the ligand, the ease of linking of the ligand to the microsphere, and the like. The manner of joining ligands to a wide variety of particles is extensively described in the literature and will not be described here.

In carrying out the method of the subject invention, a mixture of hybrid cells will be obtained after fusion between spleen cells and myeloma cells. The resulting cell mixture is grown under conditions which result in mortality of the spleen cells as well as myeloma cells, leaving a heterogenous mixture of hybridoma cells capable of producing a wide variety of antibodies. In the subsequent stages, media for the hybridoma cells are employed which maintain the cells viability. Conventional nutrient media containing appropriate protein levels e.g. 15% FCS may be employed.

The ligand-coupled fluorescent microspheres are dispersed, conveniently by sonication, in a medium and combined with a sufficient number of cells to provide for the likelihood of the desired cell(s) being present and permitting a plurality of microspheres to bind to a single cell. Conveniently, from about $1 \times 10^4$ to about $1 \times 10^7$, more usually about $1 \times 10^5$ to $1 \times 10^6$ cells are employed per 100 μg of microspheres in a convenient volume, generally being from about 0.5 to 2 ml. The microspheres and cells are combined under conditions maintaining the viability of the cells, so that during subsequent processing, the cells remain viable. Conveniently, fetal calf serum or its equivalent will be employed in the medium, conventionally at about 15%.

After combining the microspheres and cells, it is desirable to centrifuge the mixture, to provide a monolayer of the sedimented cells. In the absence of centrifugation or other means for sedimenting the cells, it is found that there is little evidence of the specific binding of the microspheres to the cells.

The centrifugation is carried out at a g value which minimizes breakage of the membrane, so as to inhibit cell destruction. Usually, this will be from about 250 to 1000 g, preferably about 500 g, for from about 5 to 30 min., conveniently under ambient conditions. Desirably, the monolayer is allowed to stand (incubate) for about 5 to 60 min., followed by washing of the cells to remove unbound microspheres.

The desired cells may now be sorted for the viable cells having the antibodies of interest. The binding of the microspheres to the cells will be indicative of the presence of the desired antibodies, but other techniques can be used for determining viability. The use of a fluorescent-activated cell sorter allows for determination of light scattering and autogenous fluorescence, where the viable cell provides for substantially greater light scatter than the dead cell, while the dead cell provides for greater autogenous fluorescence (red) than the viable cell.

As indicated previously, while fluorescence is the preferred method for activating the cell sorter, other labels may also be used which provide for differentiation between cells to which particles are bound and cells to which no particles are bound. The significant factor is a label which allows for nondestructive separation of the cell to which the particle is bound. By providing for a detector system which distinguishes between labeled cells and unlabeled cells, one can segregate a single cell into a well or other receiver and clone the cell so as to provide a source of monoclonal antibodies.

The following examples are offered by way of illustration and not by way of limitation.

Hybrid Cells

The hybrid cells used in this work were produced by fusion of the NS-1 variant of the mouse P3 (MOPC-21) myeloma line with spleen cells from mice immunized with the antigen of interest. Details of the hybridization procedures are described elsewhere (Herzenberg, supra). The production and characterization of hybrids producing antibody to mouse immunoglobulin allotypes and to molecules in the major histocompatibility complex, including clones Ig(1b)2.4 and 11–5.2 used in this work, have been described by Oi et al., (1978) Curr. Top. Microbiol. Immunol. 81, 115–129. The cells were cultured in RPMI-1640 medium (GIBCO) containing 15% fetal calf serum. Incubation was at 37° C. in an atmosphere containing 7% $CO_2$.

Four distinct cell populations were used in this work.

(i) Clone Ig(1b)2.4 secretes $IgG_3$ antibody with Ig-1b($IgG_{2a}$ of the b allotype) reactivity. It was produced through immunization of BALB/c mice with C57BL/20 ($Ig^b$) Bordetella pertussis-anti-B. pertussis complexes. A subclone of this, Ig(1b)2.4.12, was also used.

(ii) Clone 11–5.2 produces antibody to I-$A^k$, the product of a locus of the I-$A^k$ halotype of the murine major histocompatibility complex. The spleen cell donor was a BALB/c (H-$2^d$, $Ig^a$) immunized with CKB(H-$2^k$,$Ig^b$) spleen cells.

(iii) Uncloned population 20-6 was derived from an immunization of SJL mice with BALB/c Ig (a allotype) in the form of B. pertussis-anti-B. pertussis complexes. It secretes Ig-1b($IgG_{2a}$) antibody with reactivity to Ig-1a. Clone 20-6.B6 was also used in this work.

(iv) Uncloned population 20-9 was derived from the same hybridization as 20-6. It produces antibody reacting with BALB/c Ig and with MOPC-21 ($IgG_1$, a allotype) myeloma protein.

Antigen-Coupled Microspheres

Polymeric microspheres of 0.783-μm diameter were obtained from Polysciences, Inc. (no. 7766, Warrington, PA). They are blue-green fluorescent (excitation peak at 465 nm and emission peak at 485 nm) and have carboxyl groups on their surface.

Myeloma proteins for use as Ig allotype antigens were obtained by affinity chromatography on Sepharose-*Staphylococcus aureus* protein A (Pharmacia).

Myeloma proteins GPC-8 (Ig-1a) and C.BPC-101 (Ig-1b) were coupled to the fluorescent microspheres by a carbodiimide reaction (Hoare and Koshland (1967) J. Biol. Chem. 242, 2447). Roughly 40% of added $^{125}I$-labeled myeloma protein (originally 5 mg per 100 mg of microspheres) was coupled to the microspheres, indicating about 25,000 IgG molecules per microsphere. The microspheres were dispersed by sonication before use.

Cell Labeling with Antigen-Coupled Microspheres

Hybridoma cells were washed and mixed with microspheres in 24-well culture trays (Costar No. 3524, flat-bottomed wells, 16 mm in diameter, Cambridge, MA). Each well normally contained $5 \times 10^5$ cells and 100 µg of microspheres in 1 ml of RPMI-1640 with 15% non-heat-inactivated fetal calf serum. The trays were centrifuged at 500 xg for 15 min., sedimenting the cells and microspheres together on the tray bottom in approximately a monolayer. After 15–30 min at room temperature the cells were washed to remove unbound microspheres by centrifugation at 60 xg through a layer of fetal calf serum.

Assay for Secreted Antibody

Antibody binding to myeloma protein C.BPC-101 or GPC-8 was measured in a solid-phase radioimmunoassay.

Cell Sample Analysis and Sorting

Quantitative fluorescence analysis and cell sorting (Bonner et al. (1971) Rev. Sci. Instrum. 43, 404–409) were performed using a FACS-II cell sorter (Becton Dickinson FACS Division, Mountain View, CA). It measures forward-angle light scatter and two channels of fluorescence on a cell-by-cell basis. It was also employed to sort one viable cell per well in 96-well plates (cloning) on the basis of light scattering and fluorescence properties of the cell. Use of the FACS-II for cloning involved modifications that are described below.

FACS measurements were made using the 488-nm argon ion laser line at a power of 0.40 W. Long-pass filters were used to block scattered laser light while passing fluorescent light. The laser line and filter combination used are far from the optimum for exciting and detecting the microsphere fluorescence, but because the fluorescence of single microspheres was easily measured, there was no need for optimization. The fluorescent light was divided between two photomultiplier tube detectors by a chromatic reflector (LP580, No. 466305, Zeiss), which reflects light with wavelengths shorter than 580 nm and passes longer-wavelength light. The two fluorescence signals are combined linearly to yield independent quantitative measurement of two fluorescent signals from each cell. (Loken et al. (1977) J. Histochem. Cytochem. 25, 899–907).

In a first experiment, the specificity of binding of antigen-coupled microspheres to viable cells of two clonally derived hybrid cell lines was investigated. One line, 20-6, B6, produces antibody reactive with determinants on the BALB/c $IgG_{2A}$ myeloma protein GPC-8 (which carries Ig-1a allotype determinants) while the other line, Ig(1b) 2.4.12, produces antibody reactive with Ig-1b allotypic determinants on the CB.20 $IgG_{2a}$ myeloma protein C.BPC-101. Each cell line specifically binds microspheres coupled to its reactive antigen; the anti-Ig-1a lines binds an average of 44 GPC-8-coupled microspheres per cell, but only 0.4 C.BPC-101 microspheres, and the anti-Ig-1b line binds 21 C.BPC-101 microspheres but only 0.2GPC-8 microspheres. Only 4.7% of the Ig(1b) 2.4.12 cells carried even 1 GPC-8 microsphere.

In the next experiment, as a convenience in cloning cells, it is desirable in cell sorting to include a further parameter which distinguishes between live and dead cells. By combining forward-angle light scattering measurements with red fluorescence, where the former is indicative of live cells, and the latter is indicative of dead cells, one can further distinguish viable hybridoma from non-viable hybridoma cells. Thus, the cells selected will have a high probability of being viable hybridoma cells producing the desired antibody. In effect viable cells sorted by light scatter and autofluorescence (red) signals can then be further sorted according to number of microspheres using the other (green) fluorescence channel of the FACS.

In order to deflect a single viable cell binding a selected number of microspheres per (micro)culture, the FACS was reversibly modified to provide that undeflected drops from the liquid jet are intercepted and aspirated away, while after a signal from the FACS operator one cell meeting preset light scatter, autofluorescence, and microsphere criteria, is deflected into a well of a 96-well microculture tray. The wells of the tray were prefilled with 0.1 ml of culture medium containing $10^6$ thymocytes as feeder cells. Between deflections, the culture tray was moved manually to target the next well. Asepsis was readily maintained.

Several experiments were performed providing practical demonstrations of the specificity of hybrid cell labeling with antigen-coupled microspheres and the ability of the FACS to select and directly clone rare cells. In each case, cells producing antibody with reactivity for a particular myeloma protein were mixed, at a frequency of 1 in 500, with cells producing some other antibody. The rare cells were then recovered by labeling with appropriate antigen-coupled microspheres and sorting the brightly labeled cells with the FACS.

In one experiment Ig(1b) 2.4 cells producing antibody to Ig-1b were mixed with 11-5.2 cells producing antibody to the $IA^k$ cell surface antigen. The mixture was labeled with C.BPC-101 (Ig-1b) coupled microspheres and the brightest 0.27% of viable cells those binding more than 8 microspheres) were selectively segregated. Eleven out of 18 clones tested were found to secrete antibody to Ig-1b. This is an enrichment of over 250-fold from the original 1:500 mixture.

To control for possible difference in cloning efficiency between the different cells in a mixture, a similar experiment was performed by using microscopic analysis immediately after sorting rather than culturing to measure the frequency of desired cells in the sorted population. The rare cells in the mixture were prelabled with the DNA-specific fluorescent dye fixed with Hoecht 33342. This compound fluoresces at a wavelength 335 nm which does not interfere with the excitation of the fluorescent microspheres. Two mixtures were sorted and analyzed: In one case the Ig(1b) 2.4 cells were prelabeled and mixed with anti-I-$A^k$-producing cells (clone 11-5.2); in the other anti-Ig-1a-producing cells (20-6) were prelabeled and mixture with cells (20-9) producing antibody to MOPC-21, an $IgG_1$ myeloma. The first mixture was then labeled with Ig-1b (C.BPC-101) microspheres and the second was labeled with Ig-1a (GPC-8) microspheres. In each case the brightest 0.2% of cells were sorted into small wells on a microscope slide (the first mixture yielded 77 Hoecht 33342-labeled cells out of 142 or 62% and the second yielded 29 prelabeled cells out of 85 or 46%). Thus these tests also show an enrichment factor of about 250.

In accordance with the subject invention, a sensitive, accurate and rapid method is provided for selecting cells producing a specific antibody, where the cells remain viable and can then be used to clone for production of monoclonal antibodies. Since cell sorters can examine 2,000 or more cells per second, a relatively large number of desired cells can be obtained within a short time to insure the preservation of at least one clone providing the desired antibodies.

Although the foregoing invention has been described in some detail by way of illustration and example for purposes of clarity of understanding, it will be obvious that certain changes and modifications may be practiced within the scope of the appended claims.

What is claimed is:

1. A method for selectively isolating a hybridoma cell producing antibodies to a specific determinant site which comprises:

combining a heterogeneous mixture of hybridoma cells producing a variety of antibodies including an antibody for said determinant site with said determinant site bound fluorescent labeled microspheres, wherein said label permits mechanical selection of cells labeled with said microspheres as compared to cells which are unlabeled;

centrifuging said mixture of hybridoma cells and microspheres to provide a monolayer of sedimented cells, followed by separating bound microspheres from unbound microspheres;

selectively segregating by means of said microsphere label from cells having fewer microspheres than said predetermined number individual cells labeled with said microspheres at a predetermined minimum number of microspheres per cell; and growing said selectively segregated cell.

2. A method according to claim 1, wherein said segregation employs a fluorescence activated cell sorter.

3. A method according to any of claims 1 to 2, wherein said cells are further selectively segregated by a level of light scattering and endogeneous red fluorescence to selectively segregate live from dead cells.

4. A method according to claim 1, wherein said microspheres are organic polymer microspheres of from about 0.1 to 2 micrometer diameter having fluorescent chromophore functionalities having excitation at greater than 450 nm.

5. A method for producing specific monoclonal antibodies which comprises:

combining a heterogeneous mixture of hybridoma cells capable of producing a variety of antibodies including said specific monoclonal antibodies with a mixture of fluorescent microspheres, capable of excitation above about 450 nm and to which the homologous determinant site for said monoclonal antibodies is covalently bonded, wherein said microspheres are coated with sufficient protein to inhibit aggregation;

centrifuging the mixture of microspheres and hybridoma cells to produce a cell layer;

incubating said cell layer;

separating unbound microspheres from said cell layer;

selectively segregating cells having a minimum of a predetermined number of microspheres bound to said cells from cells having fewer bound microspheres; and growing said selectively segregated cells to produce said monoclonal antibody.

* * * * *